United States Patent [19]

Inagaki et al.

[11] Patent Number: 4,927,817

[45] Date of Patent: May 22, 1990

[54] PREVENTIVE AND THERAPEUTIC AGENT AGAINST LIVER DISORDER

[75] Inventors: Tetsuya Inagaki; Eijiro Tagashira, both of Saitama; Masahiro Takaya, Shiga; Yasuhiro Nishimura, Osaka, all of Japan

[73] Assignees: Zeria Pharmaceutical Co., Ltd., Tokyo; Hamari Chemicals, Ltd., Osaka, both of Japan

[21] Appl. No.: 295,204

[22] PCT Filed: Jul. 2, 1987

[86] PCT No.: PCT/JP87/00460

§ 371 Date: Dec. 27, 1988

§ 102(e) Date: Dec. 27, 1988

[87] PCT Pub. No.: WO88/00048

PCT Pub. Date: Jan. 14, 1988

[30] Foreign Application Priority Data

Jul. 3, 1986 [JP] Japan .................................. 61-155088

[51] Int. Cl.$^5$ ............................................. A61K 31/555
[52] U.S. Cl. .................................................... 514/184
[58] Field of Search ........................................ 514/184

[56] References Cited

PUBLICATIONS

Chem. Abst. 101-110,915p, (1984).
Chem. Abst. 102-204,305n, (1985).

*Primary Examiner*—Stanley J. Friedman
*Attorney, Agent, or Firm*—Scrivener and Clarke

[57] ABSTRACT

A new preventive and therapeutic agent given by oral administration containing carnosine zinc salt as the effective component and, effective against alcoholic liver disorder, viral hepatitis or liver disorders caused by drugs, toxicants, radiation, etc.

4 Claims, No Drawings

PREVENTIVE AND THERAPEUTIC AGENT AGAINST LIVER DISORDER

TECHNICAL FIELD

The present invention relates to a new preventive and therapeutic agent against liver disorder (hepatopathy), which is particularly effective for the prevention and treatment against alcoholic liver disorder, viral hepatitis and liver disorders caused by drugs, toxic substances, radiation, etc.

BACKGROUND ART

The liver is the largest organ in human body and fulfills the most important functions such as metabolism and storage of nutritional substances, detoxicating various substances, etc. The liver maintains circulatory dynamics under normal conditions as a circulatory system next to systemic circulation and pulmonary circulation. Therefore, when hepatic cells are adversely affected either acutely or chronically by causes such as toxic substances, drugs, alcohol, viruses, etc. passing through the liver or by malnutrition, radiation, cholestasia, etc., the entire body is adversely affected.

In liver disorder, characteristic changes are observed from clinical, biochemical and histological viewpoints.

Liver disorder is characterized by increase of hepatic enzymes such as glutamic pyruvic transaminase ("GPT"), glutamic oxaloacetic transaminase ("GOT"), alkaline phosphatase ("AL-P"), sorbitol dehydrogenase ("SDH"), etc. in blood or by increase of serum bilirubin.

Measurements of activity of hepatic enzyme and bilirubin value in blood are utilized for characterization and judgment of degrees of liver disorder, and these methods are generally used for clinical examination. For example, increase of serum AL-P activity suggests physical blocking of extrahepatic bile duct, early development of liver cirrhosis or arrest of choleresis by drug. Increases of activity of serum GPT, GOT and SDH are common to all types of liver disorder and indicate damage of hepatic cells (Merk Manual, 13th edition, Chapter 8, p. 836, 1977).

Liver disorder is associated with necrosis of hepatic cells, and this necrosis is histologically identifiable and provides excellent indices to show degree of liver disorder.

Since the degree of liver disorder can be judged by conditions of hepatic enzymes in blood, serum bilirubin and necrosis of hepatic cells, these indices are generally used in search of preventive and therapeutic agents against liver disorder. Various models of hepatitis have been developed for experimental evaluation of hepatic disorder. Of these models, the liver disorder caused by hepatic toxicants such as D-galactosamine, carbon tetrachloride, etc. are most akin to the viral hepatitis or the hepatitis caused by drug, toxicants, etc. as actually seen.

In the hepatic disorder caused by carbon tetrachloride, the linkage of carbon tetrachloride is severed in liver by cytochrome P-450, thereby generating the highly toxic free radical $(.CCl_3)$, and it is generally believed that this free radical causes the disorder by combining with thiol group of protein in hepatic cell membrane or by accelerating peroxidation reaction of the lipids in cell membrane. (Biochem. pharmacol., Vol. 25, p. 2163, 1976, and Biochem. pharmacol., Vol. 21, p. 49, 1972). As the result, it biochemically induces suppression of protein synthesis in liver and escape of hepatic enzymes such as GPT, GOT and SDH into blood. Histologically, it causes coagulation necrosis, edematous degeneration and fat formation, etc.

It is said that the models with disorder caused by carbon tetrachloride and D-galactosamine are akin to the liver disorder due to chronic alcoholism. On the models with carbon tetrachloride, various descriptions have been given in literature: Amer. J. Path., Vol. 79, p. 579, 1975; Virchowa Arch, B. Cell. Path., Vol. 26, p. 331, 1978; and Semirars in Liver Disease, Vol. 1, p. 143, 1981. It is described that this model is most akin to the liver disorder caused by viruses, drugs, toxicants, etc.

As liver disorders, there are acute hepatitis, chronic hepatitis, liver cirrhosis, fatty liver, etc., and the causes are diverse such as toxicants, drugs, alcohol, viruses, malnutrition, radiation, cholestasia, etc. Various preventive and therapeutic agents have been conceived against these liver disorders. Most of these drugs were the drugs to prevent and treat the metabolic anomaly, which secondarily occurs when hepatic cells are affected, and they are disadvantageous in that the therapeutic effects against liver disorders caused by specific causes such as viruses are rather weak.

The present invention offers preventative and therapeutic agents against various types of liver disorders.

DISCLOSURE OF THE INVENTION

The present inventors have found through experiments with model animals having hepatitis experimentally induced by carbon tetrachloride that, when carnosine zinc salt was given before liver disorder occurs, the increase of hepatic enzymes in blood was effectively prevented, that it was effective to prevent liver disorder before it occured, that the same preventive effect was obtained when carnosine zinc salt was given after liver disorder had actually occurred, and that carnosine zinc salt is effective in prevention and treatment of liver disorder.

Specifically, the present invention relates to a preventive and therapeutic agent against liver disorder, containing carnosine zinc salt as effective component, and the improvement of liver disorder by carnosine zinc salt is revealed by significant decline in the increase of GPT and GOT in blood and by the reduction of the degree of necrosis of hepatic cells.

Carnosine zinc salt of the present invention is a drug known for the treatment of peptic ulcer, and its application and manufacturing method are described in the Japanese provisional patent publication No. 59-33270.

147 g of L-carnosine dissolved in 441 ml of pure water was added with a solution of 88.6 g of zinc chloride in 177 ml of pure water. 325 ml of 4N sodium hydroxide aqeous solution was dropped into said reaction solution while stirring up for 30 min., and the reaction was completed. After the reaction, the deposited precipitate was taken by filtration and was rinsed well with water until the washing solution was turned to neutral. When dried at 40° C. for 2 days, it gave 175 g of colorless powder of L-carnosine zinc salt.

The analysis result of this substance is as follows:

| | |
|---|---|
| Loss on drying (1 g; dried under reduced pressure at 60° C. for hours) | 7.63% |
| Zinc content (weight analysis) | 23.20% |
| Carnosine content (weight analysis) | 76.81% |
| Melting point | 300° C. or more |
| I.R. spectrum (KBr, $cm^{-1}$) | 3280, 1620, 1480, 1385, 1260, 1120, |

-continued 1050, 1000, 980

PREVENTION OF EXPERIMENTAL LIVER DISORDER IN RAT

EXPERIMENTAL METHOD

Carnosine zinc salt was suspended in 0.5% sodium carboxymethyl cellulose (CMC) solution to prepare 60 mg/ml and 20 mg/ml suspensions. This was given to rats orally every day for 8 days at the rate of 0.5 ml/100 g so that the dosage was to be 300 mg/kg and 100 mg/kg, respectively. To the control group, the same volume of 0.5% CMC was given.

To prepare the model animals with liver disorder caused by carbon tetrachloride, carbon tetrachloride mixed in olive oil to have a 10% (V/V) mixture was given orally at the rate of 4 ml/kg (0.4 ml/kg as carbon tetrachloride) one hour after the final administration of carnosine zinc salt or 0.5% CMC. The animals were anesthetized by intraperitoneal injection of pentobarbital at 24 hours after carbon tetrachloride was given, and blood was collected from carotid arteries. The blood was centrifuged at 3000 rpm for 15 minutes to fractionate serum, and GOT and GPT were determined (Reitman Frankel and Momose modification).

From the isolated liver, the paraffined sections were prepared, stained by H-E staining and were examined by histopathological examination.

For the experiment, male Wistar rats were used. With 10 rats in each group, they were divided into three groups: the group given with carbon tetrachloride ($CCl_4$) and 0.5% CMC only ($CCl_4$+CMC), the group given with carbon tetrachloride and 300 mg/kg or 100 mg/kg of carnosine zinc salt ($CCl_4$+carnosine zinc salt) and the group given with 0.5% CMC only (CMC).

The results are as shown in the table below:

| Specimen | Items of measurement | |
|---|---|---|
|  | GOT (KU) | GPT (KU) |
| $CCl_4$ + CMC | 2115.9 ± 260.2 | 2243.8 ± 333.0 |
| $CCl_4$ + CAZ |  |  |
| (100 mg/kg) | 2167.7 ± 777.5 | 1917.7 ± 748.6 |
| (300 mg/kg) | 629.7 ± 121.2 | 427.7 ± 69.4 |
| CMC | 89.1 ± 3.2 | 42.5 ± 1.3 |

(Note)
CAZ represents carnosine zinc salt.
KU means KARMEN unit.

The result of this experiment suggests the effect of carnosine zinc salt to prevent the experimental liver disorder caused by carbon tetrachloride.

In the acute toxicity test, female and male Wistar rats, each with body weight 150–200 g, were divided into the groups with 10 rats each, and 10 g/kg each of carnosine zinc salt was given orally. By the observation for 7 days, there was no case of death, showing very weak toxicity of this compound.

THE BEST WAY TO EXECUTE THE INVENTION

Adequate method to give carnosine zinc salt is oral administration. Dosage form may be any of suspensions, tablets, pills, capsules or powder. Though dosage of carnosine zinc salt for prevention and treatment of liver disorder may differ according to degree of liver disorder, the effective daily dosage is 0.3 mg–30 mg/kg, preferably 1.5 mg–15 mg/kg.

CAPABILITY OF EXPLOITATION IN INDUSTRY

As described above, carnosine zinc salt according to the present invention suppresses increase of GPT and GOT in blood, depending upon the dosage. In the group with 300 mg/kg administration, it was significantly decreased at risk rate of 1%.

Also, in the histopathological observation, the suppression of necrosis of hepatic cells and fat formation were observed in the group given with carnosine zinc salt.

Further, it was confirmed that acute toxicity of carnosine zinc salt of this invention is extremely weak.

Therefore, it is clear that carnosine zinc salt of this invention is effective to the model animals with liver disorder caused by carbon tetrachloride. Since these model animals with liver disorder due to carbon tetrachloride are evaluated as good models with actual liver disorder caused by viruses, drugs, toxicants, etc., it follows therefore that carnosine zinc salt of this invention is very useful as the preventive and therapeutic agent by oral administration against liver disorders.

What is claimed is:

1. The method of treating against liver disorder comprising administering orally to an individual, subject to liver disorder, an agent containing carnosine zinc salt as an effective component and in an effective amount to treat said disorder.

2. The method of claim 1 wherein said liver disorder is viral hepatitus.

3. The method of claim 1 wherein said liver disorder is caused by drugs, toxicants or radiation.

4. The method of claim 1 wherein said liver disorder is caused by alcohol.

* * * * *